(12) United States Patent
Loubens et al.

(10) Patent No.: US 8,308,764 B2
(45) Date of Patent: *Nov. 13, 2012

(54) HYPER-ELASTIC NEEDLE

(75) Inventors: Thierry Loubens, Saint-Didier au Mont d'Or (FR); Antoine Watrelot, Lyons (FR); Lionel Riou, Lyons (FR)

(73) Assignee: Soprane S.A., Lyons (FR)

( * ) Notice: Subject to any disclaimer, the term of this patent is extended or adjusted under 35 U.S.C. 154(b) by 137 days.

This patent is subject to a terminal disclaimer.

(21) Appl. No.: 12/761,784

(22) Filed: Apr. 16, 2010

(65) Prior Publication Data

US 2010/0198256 A1   Aug. 5, 2010

Related U.S. Application Data

(63) Continuation of application No. 10/181,953, filed as application No. PCT/FR01/00336 on Feb. 5, 2001, now Pat. No. 7,727,257.

(30) Foreign Application Priority Data

Feb. 4, 2000   (FR) ...................................... 00 01420

(51) Int. Cl.
   *A61B 17/06*   (2006.01)
(52) U.S. Cl. .................................................... 606/223
(58) Field of Classification Search .......... 606/222–224, 606/148
   See application file for complete search history.

(56) References Cited

U.S. PATENT DOCUMENTS

| | | | |
|---|---|---|---|
| 4,128,351 A * | 12/1978 | Kurtz et al. ................... | 606/223 |
| 4,513,747 A | 4/1985 | Smith | |
| 4,527,564 A | 7/1985 | Eguchi et al. | |
| 5,219,358 A * | 6/1993 | Bendel et al. ................... | 606/222 |
| 5,330,441 A | 7/1994 | Prasad et al. | |
| 5,342,397 A | 8/1994 | Guido | |
| 5,417,699 A | 5/1995 | Klein et al. | |
| 5,433,728 A | 7/1995 | Kim, II | |
| 5,613,974 A | 3/1997 | Andreas et al. | |
| 5,683,416 A | 11/1997 | McGregor et al. | |
| 5,749,897 A | 5/1998 | Matsutani et al. | |
| 5,779,719 A | 7/1998 | Klein et al. | |
| 5,860,991 A | 1/1999 | Klein et al. | |
| 5,904,690 A | 5/1999 | Middleman et al. | |
| 5,935,138 A | 8/1999 | McJames, II et al. | |
| 6,036,699 A | 3/2000 | Andreas et al. | |
| 6,197,035 B1 | 3/2001 | Loubens et al. | |
| 7,727,257 B2 * | 6/2010 | Loubens et al. ............... | 606/223 |

FOREIGN PATENT DOCUMENTS

| | | |
|---|---|---|
| EP | 05 296 75 | 2/1996 |
| EP | 06 496 33 | 12/1998 |
| FR | 27 645 00 | 12/1998 |
| WO | 95/08296 | 3/1995 |

* cited by examiner

*Primary Examiner* — Victor Nguyen

(74) *Attorney, Agent, or Firm* — Greenblum & Bernstein, P.L.C.

(57) ABSTRACT

A method of arranging a surgical needle in an applicator. The needle is made of a hyper-elastic alloy which, after treatment, has two distinct states and includes a crimping zone for securing a suture to the needle, a free end having a tapered point which includes an inclined heel portion arranged on an inside portion of a curved profile. The method includes forcing the needle into a roughly elongated position when the needle is housed in an internal bore of the applicator. When the needle is not housed in an internal bore of the applicator, the needle adopts a curved profile as a result of superelasticity or hyperelasticity of the needle.

23 Claims, 4 Drawing Sheets

HYPER-ELASTIC NEEDLE

CROSS-REFERENCE TO RELATED APPLICATIONS

The instant application is a continuation of U.S. patent application Ser. No. 10/181,953 filed on Feb. 5, 2001, which is a National Stage Application of International Application No. PCT/FR01/00336, filed Feb. 5, 2001. Further, the present application claims priority under 35 U.S.C. §119 of French Patent Application No. 00/01420 filed on Feb. 4, 2000. The disclosure of U.S. patent application Ser. No. 10/181,953 is hereby expressly incorporated by reference in its entirety.

BACKGROUND OF THE INVENTION

1. Field of the Invention

The present invention relates to surgical needles manufactured from hyper-elastic alloys and which are intended to be used in celioscopy or endoscopy procedures.

2. Discussion of Background Information

Patent EP 0 529 675 of Aug. 31, 1992 in the name of ETHICON INC., describes a surgical needle made of a shape memory alloy which has a low-temperature first state and a high-temperature second state.

In its low-temperature state, the needle can be configured into an elongate shape so as to allow it to be slipped into a straight tube.

In its high-temperature state, the needle forms a predetermined arc while the needle is designed to be used as a surgical needle.

The needle according to patent EP 0 529 675 is particularly well-suited to endoscopy procedures in which elements are taken to the site of surgery via a cannula or trocar which have a small-sized internal diameter.

The needle described in patent EP 0 529 675 does exhibit certain drawbacks regarding the need to bring the body of the needle arranged at the site of the operation up beside a source of heat in order to cause it to adopt a configuration which is curved into a predetermined arc.

It is also found that the tapered point of the needle runs the risk of becoming damaged inside the cannula as it is introduced to the site of the operation. What happens is that the small diameter of cannulas, approximately 5 mm, and the somewhat elongate shape of the needle, necessarily lead to its point, which is fragile, being rubbed against the interior wall of the cannula.

Damage to the tapered point of the needle is irreparable because the surgeon can no longer use it, and this forces him to introduce another needle, taking all possible skillful precautions not to damage it.

SUMMARY OF THE INVENTION

The surgical needle according to the present invention is intended to define the profile of the tapered point so that the latter does not become damaged against the interior wall of the cannula or of a special applicator of which the inside diameter housing the needle is between 1 and 2 millimeters The surgical needle according to the present invention is made of a hyper-elastic alloy which, after treatment, has two distinct states making it possible, on the one hand, to force the needle into a roughly elongate position when it is housed in the internal bore of a cannula or of an applicator and, on the other hand, when it is extracted from the cannula or from the applicator, to adopt a curved profile in the shape of an arc of a circle because of its own characteristics of superelasticity or hyper-elasticity, and in that the needle comprises, at the opposite end to the suture crimping zone, a tapered point provided with an inclined heel which is arranged inside the curvature of the needle and which bears against the interior wall of the bore of the cannula or of the applicator to protect the profile of the tapered point as said needle slides inside the internal bore.

The surgical needle according to the present invention is made of a hyper-elastic alloy which contains about 54% to 58% of nickel and about 42% to 46% of titanium.

The surgical needle according to the present invention is made of a hyper-elastic alloy which is made up essentially of nickel, titanium and a small amount of chromium, or iron, or zirconium, modifying either the transformation temperature or the hardness of the alloy.

The surgical needle according to the present invention is made of a hyper-elastic alloy which undergoes a heat treatment under stress, the temperature of which is between 400° C. and 600° C. for 15 to 60 minutes, followed by a sudden quenching in air or water at between 0° C. and 3° C.

The surgical needle according to the present invention comprises a crimping zone which is pierced with an internal blind hole intended to house a suture.

The surgical needle according to the present invention comprises a crimping zone which may, in certain cases, undergo annealing at a temperature of 500° C., followed by slow cooling, after shaping.

The surgical needle according to the present invention comprises a heel which is inclined by an angle α which depends on the internal diameter of the cannula or of the applicator, on the diameter and on the length of the needle.

The surgical needle according to the present invention has a cross-sectional profile of triangular shape, one of the vertices of which triangle constitutes the outer edge of the arc of a circle of the needle.

The surgical needle according to the present invention comprises a heel which lies on the inside of the curvature of the needle and on the opposite side to the outer edge of the triangular profile.

The surgical needle according to the present invention comprises a crimping zone which has a cross-sectional profile of circular shape.

The surgical needle according to the present invention comprises, between the crimping zone and the tapered point, a cross-sectional profile of roughly square or rectangular shape.

The invention also provides for a surgical needle comprising a crimping zone for securing a suture to the needle. The needle is made of a hyper-elastic alloy which, after treatment, has two distinct states. One of the two distinct states allows the needle to be forced into a roughly elongated position when the needle is housed in an internal bore. Another of the two distinct states allows the needle to adopt a curved profile as a result of superelasticity or hyper-elasticity of the needle. The needle has a free end comprising a tapered point which includes an inclined heel portion. The inclined heel portion is arranged on an inside portion of the curved profile. The inclined heel portion of the needle may be adapted to bear against an interior wall of the internal bore. The internal bore may be arranged in one of a cannula and an applicator. The inclined heel portion needle may be adapted to bear against an interior wall of the internal bore of the cannula or of the applicator, whereby a profile of the tapered point is protected when the needle slides inside the internal bore. The curved profile may have the shape of an arc of a circle. The free end may be located on an opposite end to an end of the needle having the crimping zone. The hyper-elastic alloy may contain between about 54% and about 58% of nickel and between about 42% and about 46% of titanium. The hyper-elastic alloy may be essentially made up of nickel, titanium and a small amount of other material. The small amount of other material may comprise at least one of chromium, iron, and zirconium. The small amount of other material may modify at least one of a transformation temperature and a hardness of the hyper-elastic alloy.

The hyper-elastic alloy may be formed by a heat treatment under stress, a temperature of which is between 400° C. and 600° C. for 15 to 60 minutes, followed by a sudden quenching at between 0° C. and 3° C. The sudden quenching may occur in one of air and water.

The needle may comprise an internal blind hole located in the crimping zone, the internal blind hole being adapted to receive the suture. The crimping zone may be formed by annealing at a temperature of 500° C., followed by slow cooling. The crimping zone may be formed by annealing at a temperature of 500° C. and shaping, followed by slow cooling.

The inclined heel portion may be inclined by an angle α, whereby the angle α is based on a diameter of the internal bore, and on the diameter and the length of the needle. The tapered point may comprise a cross-sectional shape that is triangular. A side of the triangular cross-sectional shape may be arranged at an outside portion of the curved profile. The inside portion of the curved profile may be arranged opposite the outside portion of the curved profile. The crimping zone may comprise a cross-sectional shape that is circular. The needle may comprise, between the crimping zone and the free end, a cross-sectional shape that is one of roughly square and roughly rectangular.

The invention also provides for a surgical needle comprising a crimping end adapted to be secured to a suture. The needle is made of a treated hyper-elastic alloy that is one of superelastic and hyper-elastic, whereby the needle is capable of assuming two distinct states. One of the two distinct states is defined by the needle's ability to be forced into a roughly elongated position. Another of the two distinct states is defined by the needle's ability to adopt a curved profile. The needle has a free end comprising a tapered point which includes an inclined heel portion. The inclined heel portion is arranged on an inside part of the curved profile.

The invention still further provides for a surgical needle having a crimping end adapted to be secured to a suture and a free end, wherein the needle comprises a treated hyper-elastic alloy material that is one of superelastic and hyper-elastic. The needle is capable of assuming first and second positions. The first position is defined by the needle being in a roughly elongated position. The second position is defined by the needle being in a curved position. The free end comprises a tapered point which includes an inclined heel portion. In the second position, the inclined heel portion is arranged on an inside curved part of the curved position.

BRIEF DESCRIPTION OF THE DRAWINGS

The description which will follow, with reference to the appended drawings which are given by way of non-limiting example, will allow a better understanding of the invention, wherein.

DETAILED DESCRIPTION OF THE INVENTION

Figure 2:
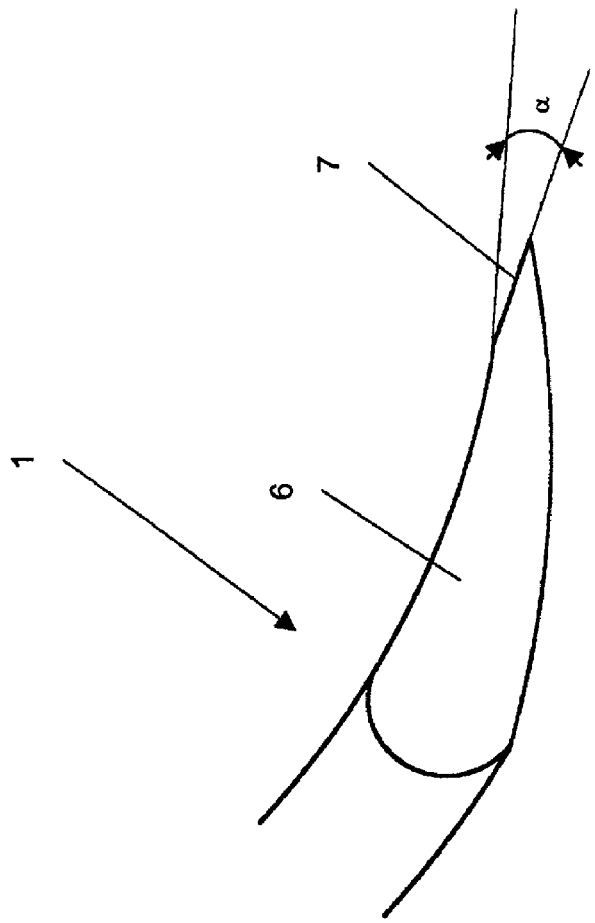
FIG. 2 is a view showing, in detail, the tapered point of the needle according to the present invention.
Figure 1:
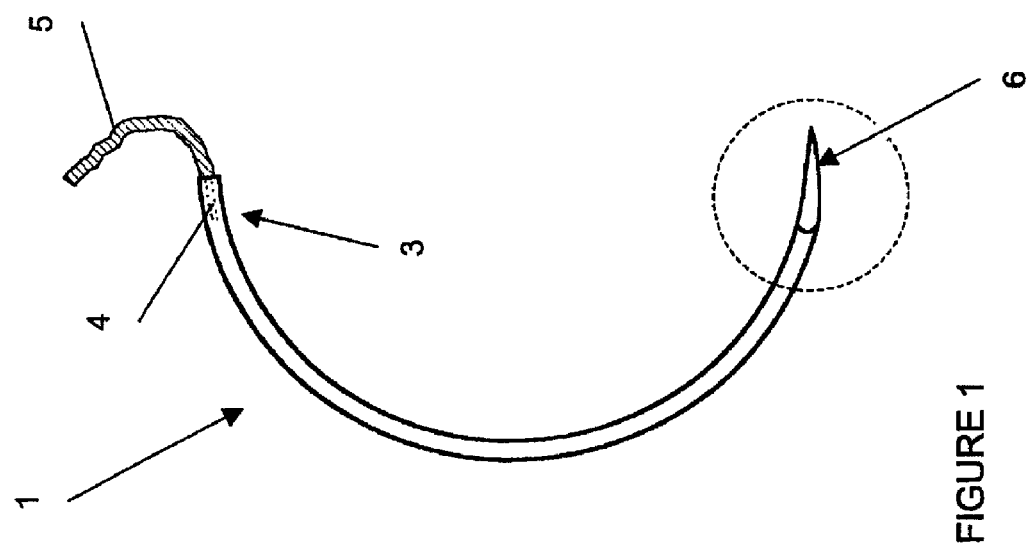
FIG. 1 is a view illustrating the needle made of hyper-elastic alloy according to the present invention.

FIGS. 1 and 2 show a needle 1 made of a hyper-elastic alloy based on nickel (Ni) and titanium (Ti) and which, after the alloy has been treated, has two distinct states.

In the first state, the needle 1 can be forced into a roughly elongate position so as to be arranged inside a cannula or applicator 2.

In the second state, that is to say when the stress is removed, the needle 1 is shaped into a profile in the shape of an arc of a circle for use at the site of the surgery.

The switch from the first state to the second is inherent in the characteristics of the alloy which is treated so that it has characteristics of superelasticity or hyper-elasticity.

The composition of the nickel/titanium alloy varies from 54% to 58% nickel, the remainder being titanium, that is to say from 42% to 46%. Other elements such as chromium (Cr), iron (Fe) and zirconium (Zr) may also be added in very small percentages to modify either the transformation temperature or the hardness.

The shaping of the needle is accomplished by applying a heat treatment under stress (400° C. to 600° C. for 15 to 60 minutes), followed by sudden quenching in air or water (0° C. to 3° C.).

The needle 1 comprises a crimping zone 3 which is pierced with an internal bind hole 4 intended to accommodate a suture 5 prior to crimping.

In certain cases, the crimping region 3 may undergo annealing (at 500° C. followed by slow cooling) after shaping. This heat treatment is intended to locally eliminate the elasticity of the alloy with a view to improving the retention of the suture 5 in the needle 1.

At the opposite end to the crimping zone 3, the needle 1 has a free end which is shaped with the profile of a tapered point 6. The tapered point 6 of the needle 1 can be thinned or have any other shape.

The tapered point 6 comprises a heel 7 which is arranged on the inside of the curvature in the shape of an arc of a circle of the needle 1.

The heel 7 is inclined by an angle α with respect to a horizontal tangent which depends on the internal diameter of the cannula or of the applicator 2, on the diameter and on the length of the needle 1.

Also, the needle 1 may be manufactured in all shapes known to the art of surgery. For example, the needle 1 may, in cross section, have a circular, square, rectangular or triangular profile.

A cross-sectional profile of triangular shape has been adopted as a preference for the tapered point 6, one of the vertices of which triangle constitutes the outer edge of the circular arc of the needle 1. In this case, the heel 7 is situated on the inside of the curvature of the needle 1 and on the opposite side to the outer edge of the triangular profile.

The needle 1 has, at the crimping zone 3, a cross-sectional profile of circular shape, whereas the remainder of the body of the needle which lies between the tapered point 6 and the said crimping zone 3 has a cross-sectional profile of roughly square or rectangular shape.

The roughly square or rectangular cross-sectional profile of the body of the needle 1 allows the surgeon to grasp it with greater ease in forceps or a needle holder.

Figure 3:
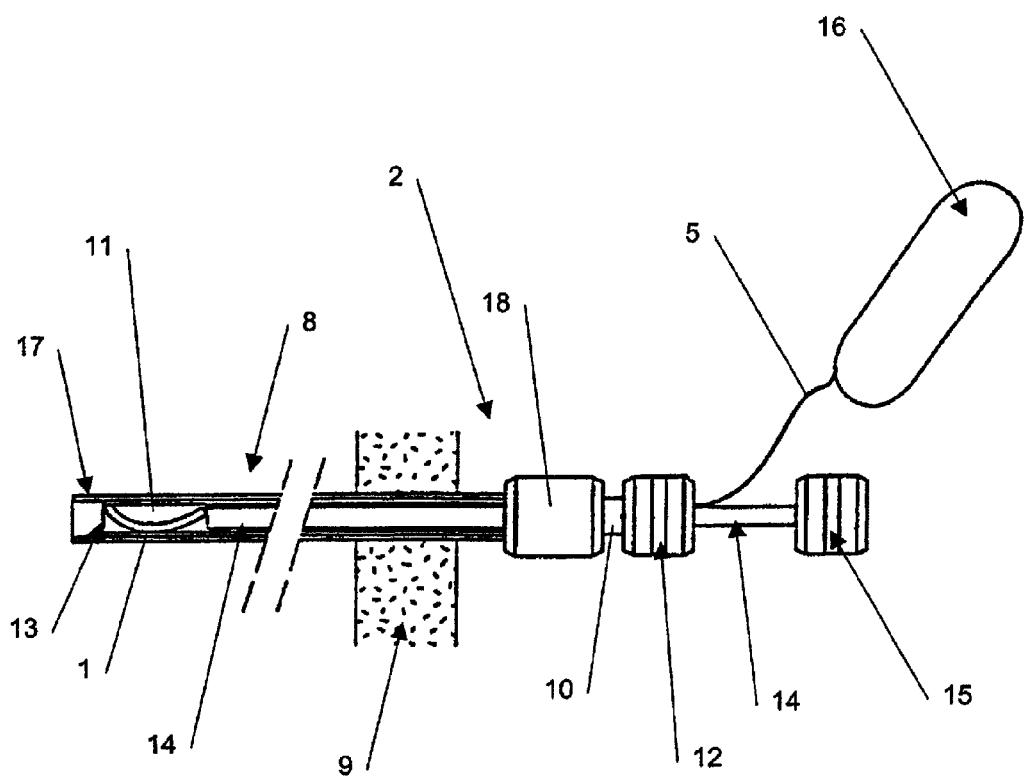
FIG. 3 is a view depicting the hyper-elastic needle forced to an elongate position inside the applicator for placement at the site of the operation.

FIG. 3 depicts the applicator 2 for the placement of the needle 1 secured to its suture 3 at the site of the surgery using a trocar 8 which has already been placed through the wall 9 of a patient.

This applicator has been described and protected in a French patent No. 97 07681 (which corresponds to U.S. Pat. No. 6,197,035) of which the applicant is the owner.

The applicator 2 comprises a cylindrical sleeve 10 pierced along its entire length and parallel to its longitudinal axis with a bore 11 in which the needle 1 and its suture 5 are housed.

The sleeve 10 comprises at one of its ends a cylindrical head 12 which is given a diameter greater than that of the remainder of the body of the sleeve.

The needle 1 is arranged in the bore 11 of the sleeve 10 in such a way that its tapered point 6 faces toward the free end 13 and away from the end with the head 12.

The applicator 2 comprises a rod 14 which is secured at one of its ends to a cylindrical stop 15.

The rod 14 is introduced into the sleeve 10 in such a way as to bear against the needle 1. The rod 14 passes through the bore 11, so that the suture 5 is arranged between the rod and the wall of the bore.

Retaining mechanism 16 allows the rod 14 to be held in position with respect to the sleeve 10, so that the free end of the rod 14 which is the opposite end to the stop 15, always presses against the needle 1.

The applicator 2 is arranged inside the trocar 8 which has already been placed through the wall 9 of a patient.

The trocar includes a tube 17 secured at one of its ends to a circular skirt 18 acting as a stop for the applicator when the needle 1 is placed at the site of the surgery as will be seen better later on.

The tube 17 of the trocar 8 is designed to accommodate the sleeve 10 of the applicator 2, while the head 12 bears against the circular skirt 18.

The surgeon then withdraws the retaining mechanism 16 in order to release the rod 14 with respect to the sleeve 10.

Figure 4:
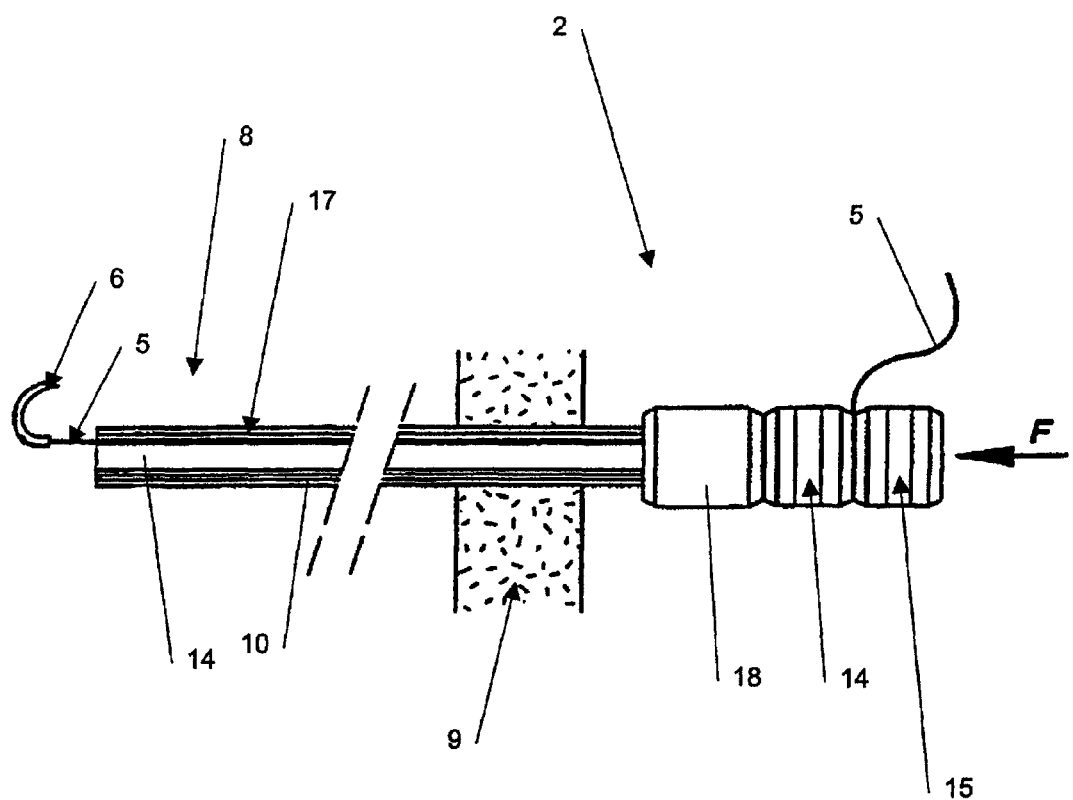
FIG. 4 is a view similar to that of FIG. 3 but illustrating the needle extracted from the applicator.

FIG. 4 shows the extraction of the needle 1 from the sleeve 10 of the applicator 2.

All the surgeon needs do is to press, in the direction of the arrow F, on the stop 15 of the rod 14, so as, via the rod 14, to push the needle 1 out of the sleeve 10. The displacement of the rod 14 is limited in its travel to the point where the stop 15 makes contact with the head 12 of the sleeve 10.

When the needle 1 is extracted from the sleeve 10 of the applicator, this needle, because of its elasticity, adopts its circular-arc shape, allowing the surgeon to suture.

Figure 5:
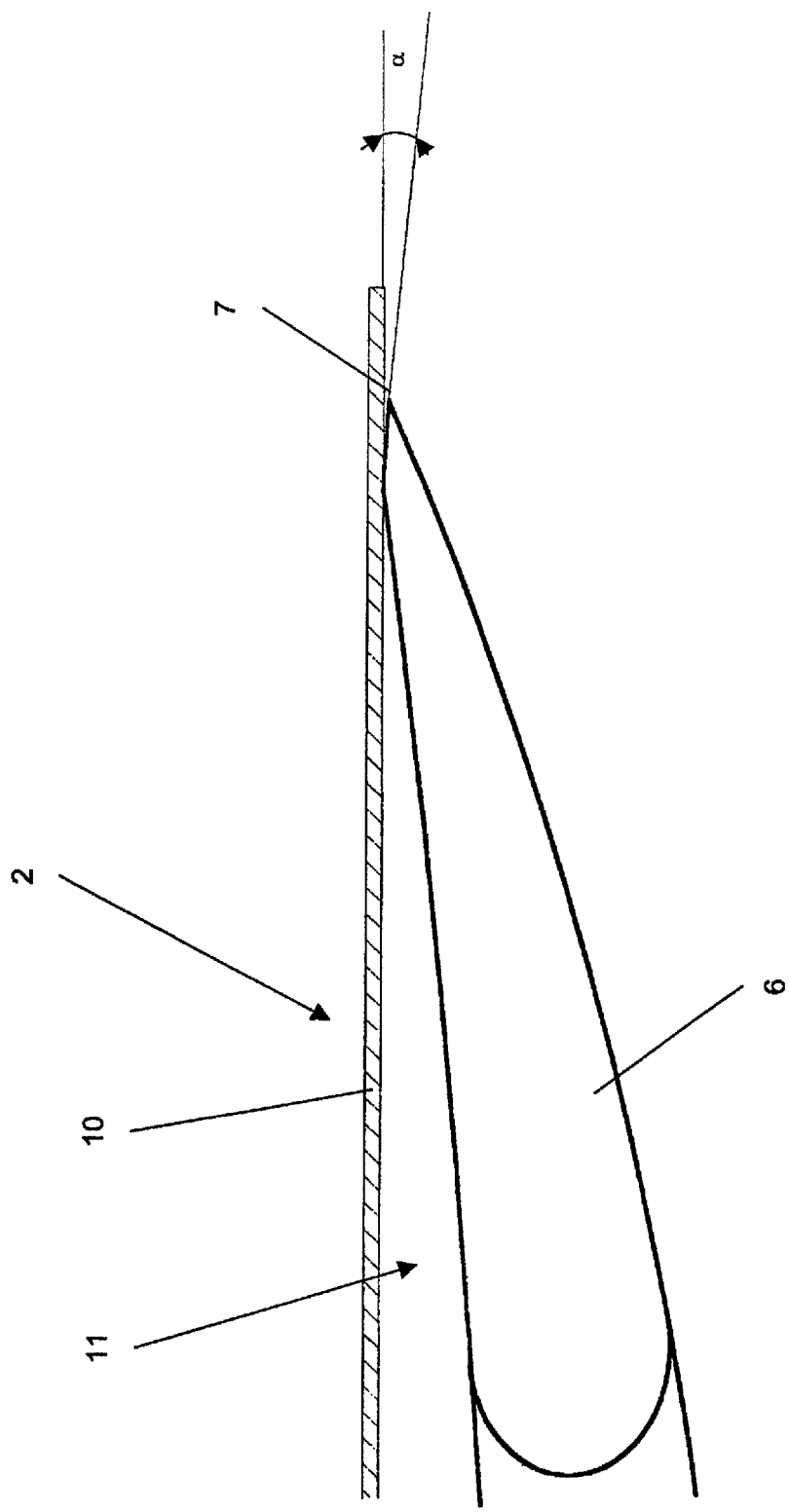
FIG. 5 is a view showing, in detail, the position at the tapered point of the needle inside the applicator.

FIG. 5 shows the position of the tapered point 6 of the needle 1 inside the bore 11 of the sleeve 10 of the applicator 2.

It can be seen that the heel 7 allows the tapered point 6 of the needle to be protected as it moves or slides inside the bore 11 of the sleeve 10.

What happens is that only the heel 7, and more particularly, the point where it meets the curved part of the needle 1, is in contact with the internal wall of the bore 11 of the sleeve 10, thus protecting the tapered point 6 against any damage due to rubbing.

It goes without saying that the applicator 2 may be replaced by a cannula or a trocar which are known per se for the placement of the needle 1 inside the operating site, without that in any way changing the subject of the present invention.

What is claimed:

1. A method of arranging a surgical needle in an applicator, wherein the needle is made of a hyper-elastic alloy which, after treatment, has two distinct states and comprises a crimping zone for securing a suture to the needle, a free end comprising a tapered point which includes an inclined heel portion arranged on an inside portion of a curved profile, the method comprising:
   forcing the needle into a roughly elongated position when the needle is housed in an internal bore of the applicator,
   wherein, when the needle is not housed in the internal bore of the applicator, the needle adopts a curved profile as a result of superelasticity or hyper-elasticity of the needle, and
   wherein, when the needle is housed in the internal bore of the applicator, the needle is configured to be pushed out of an insertion end of the applicator.

2. The method of claim 1, further comprising arranging the inclined heel portion of the needle so as to bear against an interior wall of the internal bore, whereby a profile of the tapered point is protected when the needle slides inside the internal bore.

3. The method of claim 1, wherein the curved profile has the shape of an arc of a circle.

4. The method of claim 1, wherein the free end is located on an opposite end to an end of the needle having the crimping zone.

5. The method of claim 1, wherein the hyper-elastic alloy contains between about 54% and about 58% of nickel and between about 42% and about 46% of titanium.

6. The method of claim 1, wherein the hyper-elastic alloy is essentially made up of nickel, titanium and a small amount of other material.

7. The method of claim 6, wherein the small amount of other material comprises at least one of chromium, iron, and zirconium.

8. The method of claim 6, wherein the small amount of other material modifies at least one of a transformation temperature and a hardness of the hyper-elastic alloy.

9. The method of claim 1, wherein the hyper-elastic alloy is formed using a heat treatment under stress, a temperature of which is between 400° C. and 600° C. for 15 to 60 minutes, followed by a sudden quenching at between 0° C. and 3° C.

10. The method of claim 9, wherein the sudden quenching occurs in one of air and water.

11. The method of claim 1, wherein the needle comprises an internal blind hole located in the crimping zone and the internal blind hole receives the suture.

12. The method of claim 1, wherein the crimping zone is formed by one of:
   annealing at a temperature of 500° C., followed by slow cooling; and
   annealing at a temperature of 500° C. and shaping, followed by slow cooling.

13. The method of claim 1, wherein the inclined heel portion is inclined by an angle $\alpha$, whereby the angle $\alpha$ is based on a diameter of the internal bore, and on the diameter and the length of the needle.

14. The method of claim 1, wherein the tapered point comprises a cross-sectional shape that is triangular and a side of the triangular cross-sectional shape is arranged at an outside portion of the curved profile.

15. The method of claim 14, wherein the inside portion of the curved profile is arranged opposite the outside portion of the curved profile and the crimping zone comprises a cross-sectional shape that is circular.

16. The method of claim 1, wherein the needle comprises, between the crimping zone and the free end, a cross-sectional shape that is one of roughly square and roughly rectangular.

17. The method of claim 1, wherein the tapered point comprises a triangular-shaped cross-section and the heel portion is arranged opposite one of the vertices of the triangular-shape.

18. A method of arranging a surgical needle in an applicator, wherein the needle is made of a hyper-elastic alloy which, after treatment, has two distinct states and comprises a crimping zone for securing a suture to the needle, a free end comprising a tapered point which includes an inclined heel portion arranged on an inside portion of a curved profile, the tapered point having a triangular-shaped cross-section and the heel portion being arranged opposite one of the vertices of the triangular-shape, the method comprising:
 forcing the needle into a roughly elongated position when the needle is housed in an internal bore of the applicator such that the inclined heel portion of the needle bears against an interior wall of the internal bore and a profile of the tapered point is protected when the needle slides inside the internal bore,
 wherein, when the needle is not housed in the internal bore of the applicator, the needle adopts a curved profile as a result of superelasticity or hyper-elasticity of the needle.

19. The method of claim 18, wherein the needle comprises, between the crimping zone and the free end, a cross-sectional shape that is one of roughly square and roughly rectangular.

20. The method of claim 18, wherein the needle is configured to be push out of an insertion end of the applicator.

21. A method of arranging a surgical needle in an applicator, wherein the needle is made of a hyper-elastic alloy which, after treatment, has two distinct states and comprises a crimping zone for securing a suture to the needle, a free end comprising a tapered point which includes an inclined heel portion arranged on an inside portion of a curved profile, the tapered point includes a cross-sectional shape that is triangular and a side of the triangular cross-sectional shape is arranged at an outside portion of the curved profile, and the inclined heel portion is shorter in axial length than other two sides of the tapered point, the method comprising:
 forcing the needle into a roughly elongated position when the needle is housed in an internal bore of the applicator such that the inclined heel portion of the needle bears against an interior wall of the internal bore and a profile of the tapered point is protected when the needle slides inside the internal bore,
 wherein, when the needle is not housed in the internal bore of the applicator, the needle adopts a curved profile as a result of superelasticity or hyper-elasticity of the needle.

22. The method of claim 21, wherein the needle comprises, between the crimping zone and the free end, a cross-sectional shape that is one of roughly square and roughly rectangular.

23. The method of claim 21, wherein the needle is configured to be push out of an insertion end of the applicator.

* * * * *